(12) United States Patent
Anand et al.

(10) Patent No.: US 9,717,531 B2
(45) Date of Patent: Aug. 1, 2017

(54) SPINAL CORRECTION METHOD AND SYSTEM

(71) Applicant: Warsaw Orthopedic, Inc., Warsaw, IN (US)

(72) Inventors: Neel Anand, Los Angeles, CA (US); Jeff R Justis, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 75 days.

(21) Appl. No.: 14/057,930

(22) Filed: Oct. 18, 2013

(65) Prior Publication Data

US 2015/0112392 A1    Apr. 23, 2015

(51) Int. Cl.
*A61B 17/70*    (2006.01)

(52) U.S. Cl.
CPC ...... *A61B 17/7011* (2013.01); *A61B 17/7083* (2013.01); *A61B 17/7086* (2013.01)

(58) Field of Classification Search
CPC .................................................. A61B 17/708
See application file for complete search history.

(56) References Cited

U.S. PATENT DOCUMENTS

| | | | |
|---|---|---|---|
| 4,771,767 A | 9/1988 | Steffee | |
| 5,385,565 A | 1/1995 | Ray | |
| 5,951,553 A * | 9/1999 | Betz | A61B 17/7044 606/246 |
| 6,080,156 A | 6/2000 | Asher et al. | |
| 6,090,110 A | 7/2000 | Metz-Stavenhagen | |
| 6,123,707 A | 9/2000 | Wagner | |
| 6,616,669 B2 | 9/2003 | Ogilvie et al. | |
| 6,743,231 B1 * | 6/2004 | Gray | A61B 17/7001 606/279 |
| 6,827,719 B2 * | 12/2004 | Ralph | A61B 17/7032 606/272 |
| 7,909,857 B2 | 3/2011 | Ogilvie et al. | |
| 8,007,522 B2 | 8/2011 | Hutchinson | |
| 8,043,338 B2 | 10/2011 | Dant | |
| 8,328,849 B2 | 12/2012 | Nydegger et al. | |
| 2001/0029375 A1 | 10/2001 | Betz et al. | |
| 2002/0055740 A1 | 5/2002 | Lieberman | |

(Continued)

OTHER PUBLICATIONS

Lonner, Baron S., MD, "Scoliosis Surgery Video—Adolescent Idiopathic Scoliosis, Parts 1-3", https://www.youtube.com/watch?v=t7TNUGTCpEU, https://youtu.be/A-fbOPS84U4, https://www.youtube.com/watch?v=1kvScXxV8xA, Jun. 22, 2011, transcript attached.*

*Primary Examiner* — Jan Christopher Merene (57) ABSTRACT

A method for treating a spine comprises the steps of: fastening a plurality of fasteners with a lateral portion of vertebrae, each of the fasteners including a first element that defines an implant cavity and a second element configured for penetrating the vertebrae; providing a longitudinal element including a portion having a selected curvature; disposing the longitudinal element with the implant cavities such that the portion is disposed in a selected orientation relative to the vertebrae; and moving a first element of at least one of the fasteners relative to the portion such that a second element of the at least one of the fasteners derotates the vertebrae while maintaining the portion in the selected orientation. Systems and implants are disclosed.

20 Claims, 7 Drawing Sheets

(56) References Cited

U.S. PATENT DOCUMENTS

| | | |
|---|---|---|
| 2004/0186472 A1 | 9/2004 | Lewis et al. |
| 2005/0033291 A1* | 2/2005 | Ebara ............................ 606/53 |
| 2005/0065517 A1* | 3/2005 | Chin ............................. 606/61 |
| 2005/0131405 A1 | 6/2005 | Molz et al. |
| 2005/0192570 A1* | 9/2005 | Jackson ............. A61B 17/7032 606/914 |
| 2006/0036255 A1 | 2/2006 | Pond et al. |
| 2006/0195092 A1* | 8/2006 | Barry ............................ 606/61 |
| 2006/0271050 A1* | 11/2006 | Piza Vallespir ................ 606/61 |
| 2007/0191840 A1* | 8/2007 | Pond ................. A61B 17/7085 623/17.16 |
| 2007/0213714 A1* | 9/2007 | Justis ............................ 606/61 |
| 2008/0269805 A1* | 10/2008 | Dekutoski et al. ........... 606/279 |
| 2009/0088803 A1* | 4/2009 | Justis et al. .................... 606/254 |
| 2009/0105774 A1* | 4/2009 | Jones ................ A61B 17/7083 606/86 A |
| 2010/0063548 A1 | 3/2010 | Wang |
| 2010/0312281 A1* | 12/2010 | Barry ............................ 606/264 |
| 2011/0137358 A1 | 6/2011 | Manninen |
| 2011/0172714 A1* | 7/2011 | Boachie-Adjei ... A61B 17/7086 606/264 |
| 2011/0319938 A1* | 12/2011 | Piza Vallespir et al. ..... 606/264 |

\* cited by examiner

SPINAL CORRECTION METHOD AND SYSTEM

TECHNICAL FIELD

The present disclosure generally relates to medical devices for the treatment of musculoskeletal disorders, and more particularly to a surgical system and method for correction of a spine disorder.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. Correction treatments may employ implants that are manipulated for engagement with vertebrae to position and align one or more vertebrae. This disclosure describes an improvement over these prior art technologies.

SUMMARY

In one embodiment, a method for treating a spine is provided. The method comprising the steps of; fastening a plurality of fasteners with a lateral portion of vertebrae, each of the fasteners including a first element that defines an implant cavity and a second element configured for penetrating the vertebrae; providing a longitudinal element including a portion having a selected curvature; disposing the longitudinal element with the implant cavities such that the portion is disposed in a selected orientation relative to the vertebrae; and moving a first element of at least one of the fasteners relative to the portion such that a second element of the at least one of the fasteners derotates the vertebrae while maintaining the portion in the selected orientation. In some embodiments, implants and systems are disclosed.

In one embodiment, the method comprises the steps of: fastening a plurality of fasteners with a lateral portion of vertebrae, each of the fasteners including a receiver that defines an implant cavity and a shaft configured for penetrating the vertebrae; providing a longitudinal element including a portion having a selected curvature; connecting a surgical instrument to the longitudinal element; manipulating the surgical instrument to pass the longitudinal element through the implant cavities; reducing the longitudinal element with at least one implant cavity such that the portion is disposed in a selected orientation relative to the vertebrae; and rotating a receiver of at least one of the fasteners relative to the portion such that a shaft of the at least one of the fasteners derotates the vertebrae while maintaining the portion in the selected orientation.

In one embodiment, the method comprises the steps of: fastening a plurality of fasteners with a lateral portion of vertebrae, each of the fasteners including a receiver that defines an implant cavity and a shaft configured for penetrating the vertebrae, wherein one or more of the fasteners are fastened with an apical portion of the vertebrae; providing a longitudinal element including a portion having a selected curvature; reducing the longitudinal element with the fasteners disposed with the apical portion such that the portion is disposed in a selected orientation relative to the vertebrae; moving the receivers relative to the portion such that the shafts derotate the vertebrae while maintaining the portion in the selected orientation; and subsequently reducing the longitudinal element with the remaining fasteners sequentially from the apical portion in a cephalad and/or a caudal orientation.

BRIEF DESCRIPTION OF THE DRAWINGS

The present disclosure will become more readily apparent from the specific description accompanied by the following drawings, in which.

DETAILED DESCRIPTION

The exemplary embodiments of the spinal correction system and related methods of use disclosed are discussed in terms of medical devices for the treatment of musculoskeletal disorders and more particularly, in terms of a spinal correction system and method that facilitates connection of at least one implant with vertebrae to position and align one or more vertebrae for treatment of a spine. In some embodiments, the spinal correction system can include instruments such as extenders, reducers and translators, which can be used to introduce a vertebral construct such as a rod to a bone fastener, such as a bone anchor or bone screw. For example, an instrument can include an extender having bone anchor attachment features on one or both sides of the instrument. In some embodiments, the extender may be used with or include a reducer assembly to introduce a spinal rod into a bone fastener.

In one embodiment, a method for spinal correction is provided with a system for posterior screw and rod placement and manipulation for deformity correction. The method includes use of multi-axial or poly-axial pedicle screws placed minimally invasively with a removable slotted extension that guides placement of a longitudinal rod with a selected sagittal curve to control spine curvature in lower thoracic and lumbar regions. In one embodiment, the method employs minimally invasive direct lateral interbody techniques that allow coronal plane deformity correction prior to posterior screw/rod placement. In some embodiments, interbody implants, bone screws and spinal rods are provided as a stable construct for deformity correction and fusion.

In one embodiment, the method allows direct correction of a sagittal plane deformity through contouring of one or more spinal rods. In one embodiment, the method provides coronal plane deformity correction by maintaining the sagittal plane curvature of the spinal rods parallel to the sagittal plane after rod placement through screw extensions. The spinal rods are reduced vertically through screw extenders and a screw head of the poly-axial screws are pivoted around an outer surface of the spinal rods to provide coronal plane correction and/or provide derotation of vertebral bodies.

In one embodiment, the system is employed with a method for deformity correction, such as, for example, correction of an adolescent idiopathic scoliosis using a construct of implants including fasteners, such as, for example, multi-axial pedicle screws, and manipulating the implants using implant supports, such as, for example, reduction instruments. In one embodiment, the system is employed with a method for deformity correction, such as, for example, correction of a lumbar scoliosis. In some embodiments, the system is employed with a method and sequence to efficiently correct various deformity pathologies in sagittal, coronal and axial planes of vertebrae by using screws and reduction instruments.

In some embodiments, vertebrae can be derotated using surgical instruments and fasteners as a lever prior to final tightening of set screws with the fasteners. For example, this derotation can be performed initially at the apex of a disorder and then cephalad and caudal from a mid-portion of a pre-formed spinal rod. Such derotation can be performed segmentally and/or prior to final tightening.

In some embodiments, the system is employed for axial derotation of vertebral bodies to improve chest wall volume and pulmonary function. In one embodiment, the system includes pedicle screws placed in the vertebral bodies that provide anchors for spinal manipulation. In one embodiment, the system includes implant supports, such as, for example, reduction instruments attached to the pedicle screws that are configured as derotation levers and can be linked together to distribute derotation forces applied to components of the system. In some embodiments, the spinal correction system may include instruments that are connected or attached to an instrument(s) such as, for example, a lateral translation handle or derotation instruments.

In some embodiments, the method is used with surgical navigation, such as, for example, fluoroscope or image guidance. In one embodiment, one or all of the components of the surgical system are disposable, peel-pack, pre-packed sterile devices. One or all of the components of the surgical system may be reusable. The surgical system may be configured as a kit with multiple sized and configured components.

In one embodiment, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In one embodiment, the present disclosure may be employed with other osteal and bone related applications, including those associated with diagnostics and therapeutics. In some embodiments, the disclosed surgical system and methods may be alternatively employed in a surgical treatment with a patient in a prone, supine position, lateral and/or employ various surgical approaches to the spine, including anterior, posterior, posterior mid-line, direct lateral, postero-lateral, and/or antero-lateral approaches, and in other body regions. The present disclosure may also be alternatively employed with procedures for treating the lumbar, cervical, thoracic, sacral and pelvic regions of a spinal column. The system and methods of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, micro discectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference will now be made in detail to the exemplary embodiments of the present disclosure, which are illustrated in the accompanying figures. Turning to FIGS. 1-7, there are illustrated components of a surgical system, such as, for example, a spinal correction system 10.

The components of spinal correction system 10 can be fabricated from biologically acceptable materials suitable for medical applications, including metals, synthetic polymers, ceramics and bone material and/or their composites, depending on the particular application and/or preference of a medical practitioner. For example, the components of spinal correction system 10, individually or collectively, can be fabricated from materials such as stainless steel alloys, commercially pure titanium, titanium alloys, Grade 5 titanium, superelastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate such as hydroxyapatite (HA), corraline HA, biphasic calcium phosphate, tricalcium phosphate, or fluorapatite, tri-calcium phosphate (TCP), HA-TCP, calcium sulfate, or other resorbable polymers such as polyaelide, polyglycolide, polyiyrosine carbonate, polycaroplaetohe and their combinations, biocompatible ceramics, mineralized collagen, bioactive glasses, porous metals, bone particles, bone fibers, morselized bone chips, bone morphogenetic proteins (BMP), such as BMP-2, BMP-4, BMP-7, rhBMP-2, or rhBMP-7, demineralized bone matrix (DBM), transforming growth factors (TGF, e.g., TGF-β), osteoblast cells, growth and differentiation factor (GDF), insulin-like growth factor 1, platelet-derived growth factor, fibroblast growth factor, or any combination thereof.

Various components of spinal correction system 10 may have material composites, including the above materials, to achieve various desired characteristics such as strength, rigidity, elasticity, compliance, biomechanical performance, durability and radiolucency or imaging preference. The components of spinal correction system 10, individually or collectively, may also be fabricated from a heterogeneous material such as a combination of two or more of the above-described materials. The components of spinal correction system 10 may be monolithically formed, integrally connected or include fastening elements and/or instruments, as described herein.

Spinal correction system 10 is employed, for example, with a minimally invasive procedure, including percutaneous techniques, and mini-open surgical techniques to deliver and introduce instrumentation and/or an implant, such as, for example, a bone fastener, for a correction treatment at a surgical site within a body of a patient, for example, a section of a spine to treat various spine pathologies, such as, for example, adolescent idiopathic scoliosis and Scheuermann's kyphosis. In some embodiments, spinal correction system 10 may comprise various instruments, such as, for example, inserters, reducers, spreaders, distracters, blades, clamps, forceps, elevators and drills, which may be alternately sized and dimensioned, and arranged as a kit.

Figure 1:
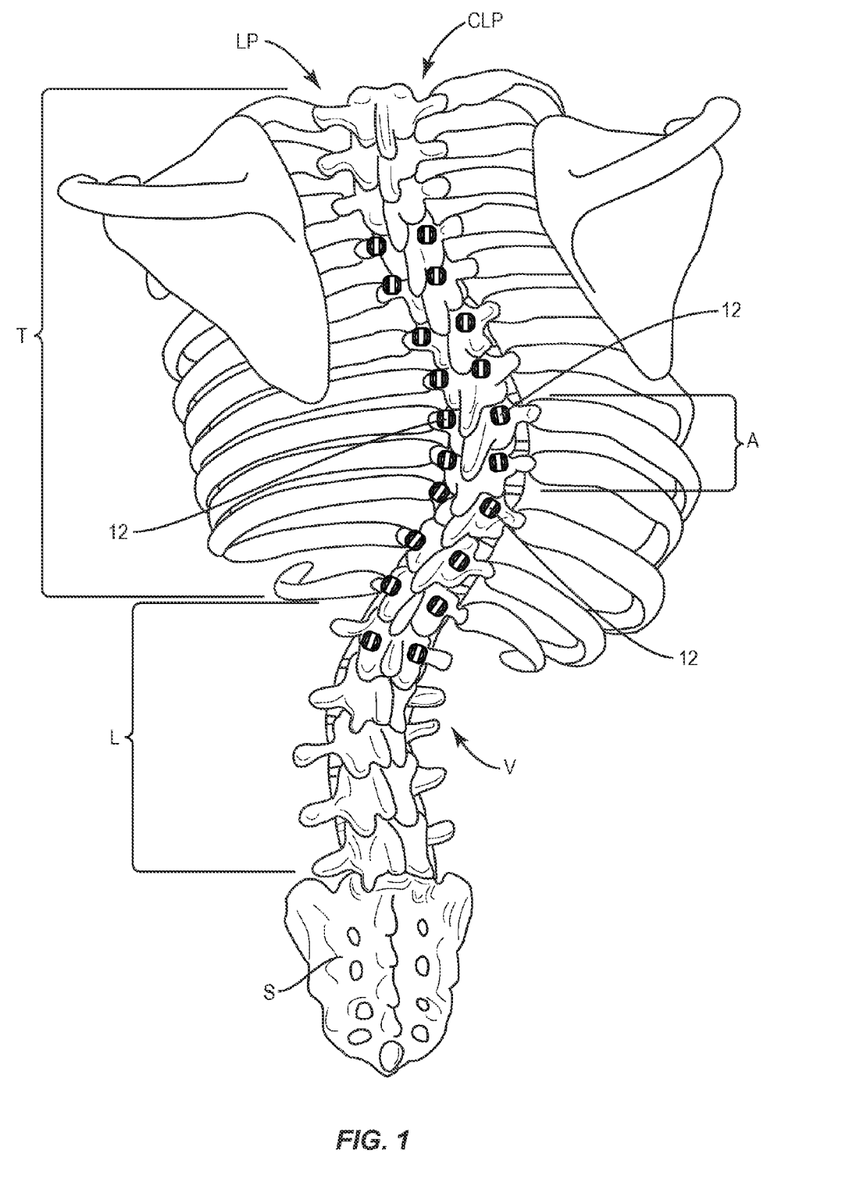
FIG. 1 is a plan view of components of one embodiment of a system in accordance with the principles of the present disclosure disposed with vertebrae of a body.
Figure 2:
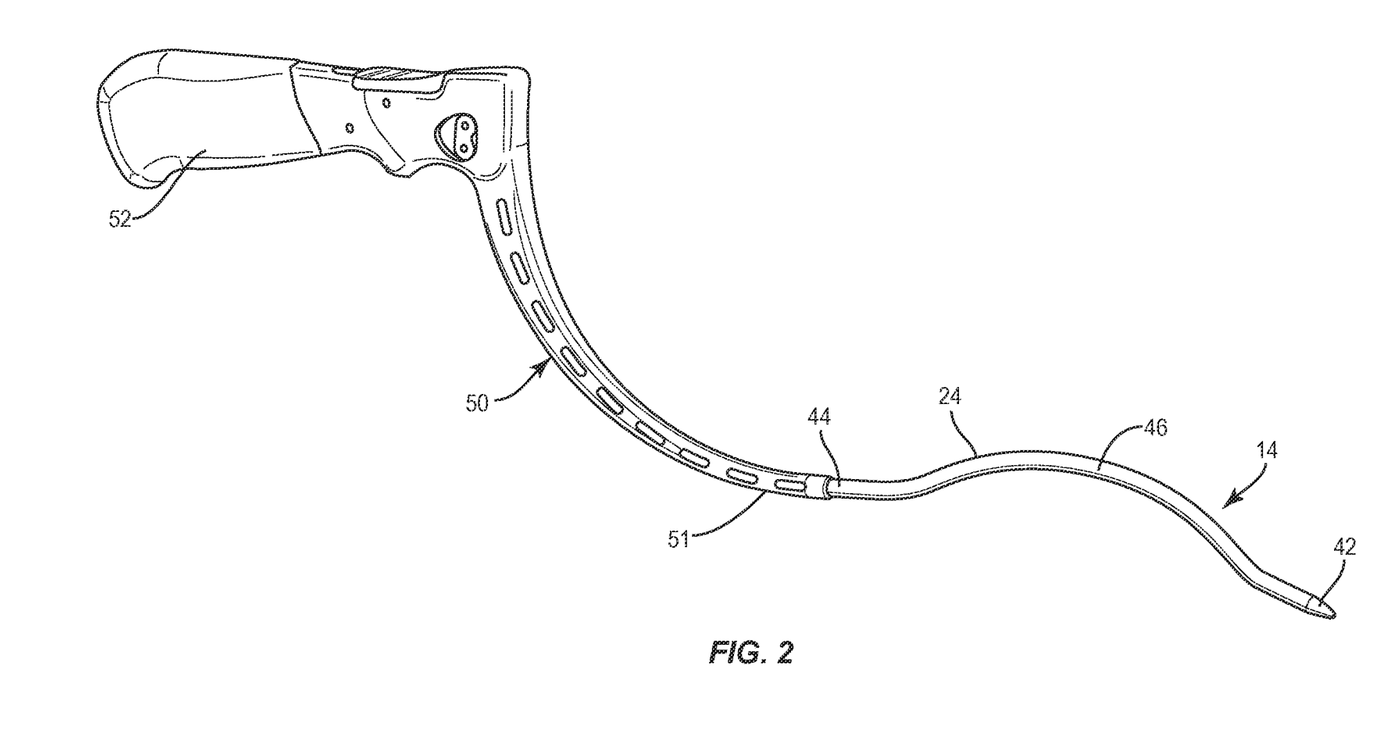
FIG. 2 is a perspective view of components of one embodiment of a system in accordance with the principles of the present disclosure.
Figure 5:
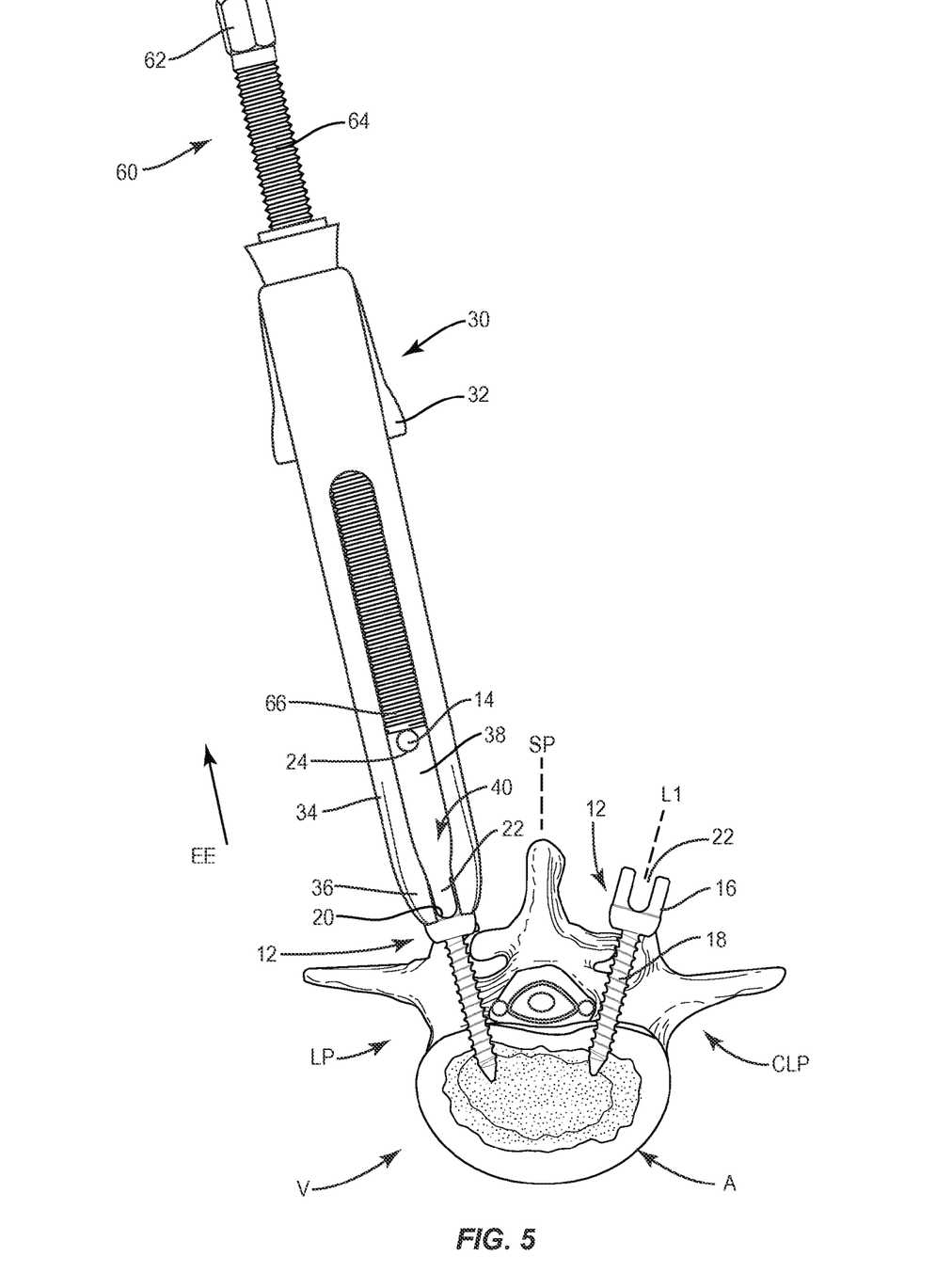
FIG. 5 is an axial view of components of the system and vertebrae shown in FIG. 3.

Spinal correction system 10 includes a fastener, such as, for example, a poly-axial or multi-axial bone screw (MAS) 12, as shown in FIG. 1, that connects a longitudinal element, such as, for example, a spinal rod 14, as shown in FIG. 2, to tissue, such as, for example, vertebrae V and/or components of spinal correction system 10, such as, for example, connectors, plates and other constructs, as will be described. Each MAS 12 defines a longitudinal axis L1, as shown in FIG. 5. MAS 12 comprises a first element, such as, for example, a receiver 16 and a second element, such as, for example, an elongated shaft 18 configured for penetrating tissue.

Shaft 18 has a cylindrical cross section configuration and includes an outer surface having an external thread form. In some embodiments, the external thread form may include a single thread turn or a plurality of discrete threads. In some embodiments, other engaging structures may be located on shaft 18, such as, for example, a nail configuration, barbs, expanding elements, raised elements and/or spikes to facilitate engagement of shaft 18 with tissue, such as, for example, vertebrae V.

In some embodiments, all or only a portion of shaft 18 may have alternate cross section configurations, such as, for example, oval, oblong, triangular, square, polygonal, irregular, uniform, non-uniform, offset, staggered, undulating, arcuate, variable and/or tapered. In some embodiments, the outer surface of shaft 18 may include one or a plurality of openings. In some embodiments, all or only a portion of the outer surface of shaft 18 may have alternate surface configurations to enhance fixation with tissue such as, for example, rough, arcuate, undulating, mesh, porous, semi-porous, dimpled and/or textured. In some embodiments, all or only a portion of shaft 18 may be disposed at alternate orientations, relative to the longitudinal axis, such as, for example, transverse, perpendicular and/or other angular orientations such as acute or obtuse, co-axial and/or may be offset or staggered. In some embodiments, all or only a portion of shaft 18 may be cannulated.

Receiver 16 includes a pair of spaced apart arms having an inner surface 20 that defines an implant cavity, such as, for example, a U-shaped passageway 22. Passageway 22 is configured for disposal of an implant, such as, for example, spinal rod 14. In some embodiments, all or only a portion of passageway 22 may have alternate cross section configurations, such as, for example, oval, oblong, triangular, square, polygonal, irregular, uniform, non-uniform, offset, staggered, and/or tapered. In some embodiments, the arms of receiver 16 may be disposed at alternate orientations, relative to axis L1, such as, for example, transverse, perpendicular and/or other angular orientations such as acute or obtuse, co-axial and/or may be offset or staggered.

In one embodiment, as shown in FIGS. 1-7, MAS 12 has a multi axial configuration such that receiver 16 is rotatable to a selected angle through and within an angular range relative to axis L1 in a plurality of planes that lie in a cone configuration. The area and/or volume defined by the cone configuration is defined by the range of motion of receiver 16 about axis L1. In one embodiment, a receiver 16 is movable relative to a shaft 18 of at least one MAS 12 to derotate vertebrae V. In one embodiment, receiver 16 is rotated and/or pivoted relative to a shaft 18 of at least one MAS 12 such that inner surface 20 rotates about and relative to an outer surface 24 of spinal rod 14 to provide coronal plane correction and/or provide derotation of vertebral levels of vertebrae V, which include at least an apical portion A of a scoliosis curvature of vertebrae V, as shown in FIG. 1. Inner surface 20 includes a thread form configured for engagement with a coupling member (not shown), such as, for example, a set screw. The set screw is threaded with receiver 16 to attach, provisionally fix and/or lock spinal rod 14 with MAS 12, as described.

In some embodiments, spinal correction system 10 includes one or more of fasteners that may be engaged with tissue in various orientations, such as, for example, series, parallel, offset, staggered and/or alternate vertebral levels. In some embodiments, the fasteners may comprise sagittal angulation screws, pedicle screws, mono-axial screws, uni-planar screws, facet screws, fixed screws, tissue penetrating screws, conventional screws, expanding screws, wedges, anchors, buttons, dips, snaps, friction fittings, compressive fittings, expanding rivets, staples, nails, adhesives, posts, fixation plates and/or posts.

Spinal rod 14 has a cylindrical cross section configuration. In some embodiments, spinal correction system 10 may include one or a plurality of spinal rods, which may be relatively disposed in a side by side, irregular, uniform, non-uniform, offset and/or staggered orientation or arrangement. In some embodiments, spinal rod 14 can have a uniform thickness/diameter. In some embodiments, spinal rod 14 may have various surface configurations, such as, for example, rough, threaded for connection with surgical instruments, arcuate, undulating, dimpled, polished and/or textured. In some embodiments, the thickness defined by spinal rod 14 may be uniformly increasing or decreasing, or have alternate diameter dimensions along its length. In some embodiments, spinal rod 14 may have various cross section configurations, such as, for example, oval, oblong, triangular, rectangular, square, polygonal, irregular, uniform, non-uniform, variable and/or tapered. In some embodiments, spinal rod 14 may have various lengths. In some embodiments, the longitudinal element may include one or a plurality of tethers.

In some embodiments, the longitudinal element may have a flexible configuration and fabricated from materials, such as, for example, polyester, polyethylene, fabric, silicone, polyurethane, silicone-polyurethane copolymers, polymeric rubbers, polyolefin rubbers, elastomers, rubbers, thermoplastic elastomers, thermoset elastomers and elastomeric composites. In one embodiment, the flexibility of the longitudinal element includes movement in a lateral or side to side direction and prevents expanding and/or extension in an axial direction. In some embodiments, all or only a portion of the longitudinal element may have a semi-rigid, rigid or elastic configuration, and/or have elastic properties, such as the elastic properties corresponding to the material examples described above. In some embodiments, the longitudinal element may be compressible in an axial direction.

In assembly, operation and use, spinal correction system 10, similar to the systems described herein, is employed with a surgical procedure, such as, for example, a correction treatment to treat adolescent idiopathic scoliosis and/or Scheuermann's kyphosis of a spine. In some embodiments, one or all of the components of spinal correction system 10 can be delivered or utilized as a pre-assembled device or can be assembled in situ. Spinal correction system 10 may also be employed with other surgical procedures.

For example, spinal correction system 10 is employed with a surgical treatment for scoliosis correction of an affected section of a spinal column and adjacent areas within a body B of a patient, such as, for example, vertebrae V that includes thoracic vertebral levels T and lumbar vertebral levels L. Body B includes a lateral portion LP and a contra-lateral portion CLP. In one example, thoracic vertebral levels L include an apical portion A, which comprises an apex of a scoliosis curvature and/or deformity. In some embodiments, spinal correction system 10 may be employed with one or a plurality of vertebrae.

In use, to treat vertebrae V, a medical practitioner obtains access to a surgical site including vertebrae V in any appropriate manner, such as through incision and retraction of tissues. In some embodiments, spinal correction system 10 can be used in any existing surgical method or technique including open surgery, mini-open surgery, minimally invasive surgery and percutaneous surgical implantation, whereby vertebrae V is accessed through a mini-incision, or sleeve that provides a protected passageway to the area. Once access to the surgical site is obtained, the particular surgical procedure can be performed for treating the spine disorder.

One or a plurality of percutaneous incisions are made in body B and a cutting instrument (not shown) creates one or a plurality of surgical pathways and/or openings for implantation of components of spinal correction system 10. The percutaneous incisions are made in tissue of portions LP, CLP and disposed in a plane parallel to a sagittal plane SP, as shown in FIG. 5, of vertebrae V. The tissue of portions LP, CLP includes soft tissue comprising muscle, ligaments, tendons, cartilage and/or bone. Once access to the surgical site is obtained percutaneously, the components of spinal implant system 10 can be delivered or implanted with portions LP, CLP. A preparation instrument (not shown) can be employed to prepare tissue surfaces of vertebrae V, as well as for aspiration and irrigation of a surgical region.

Figure 3:
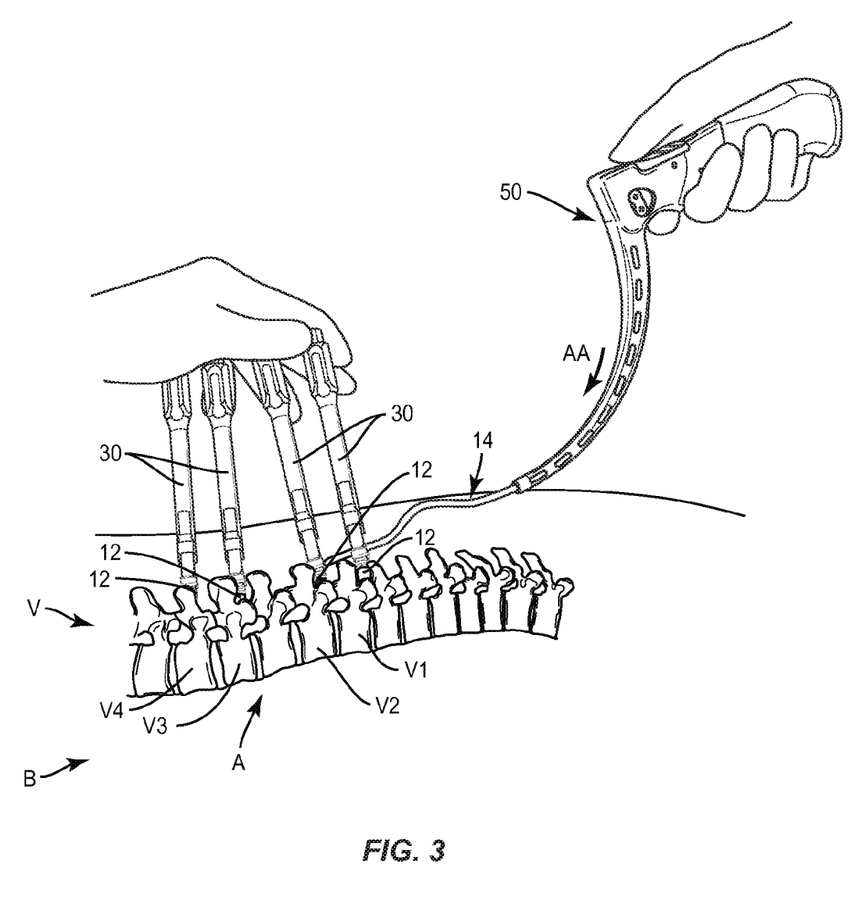
FIG. 3 is a side view of the components of the system and the body shown in FIGS. 1 and 2.
Figure 4:
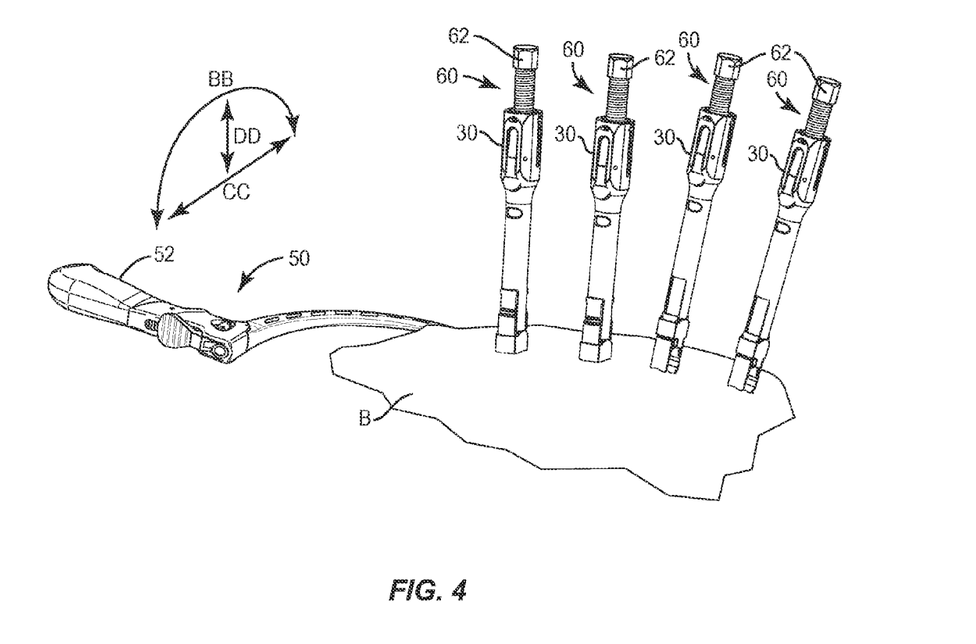
FIG. 4 is a perspective view of components of the system and the body shown in FIG. 3.

Pilot holes (not shown) are made bilaterally in vertebrae V for receiving MAS 12. Shaft 18 of each MAS 12 is inserted, drilled or otherwise fixed to the vertebral levels of vertebrae V. Spinal correction system 10 includes implant supports, such as, for example, extenders and/or reduction instruments 30 that are applied to MAS 12 attached with vertebrae V on contiguous vertebrae, as shown in FIGS. 3-5. Instruments 30 are oriented for manipulation, alignment and capture of MAS 12. In some embodiments, one or a plurality of instruments 30 can be applied to a respective concave or convex portion of vertebrae V for performing one or a plurality of steps employing spinal correction system 10. In one embodiment, instruments 30 are disposed in series along vertebrae V such that an instrument is disposed with each vertebral level of a treated section. In one embodiment, instruments 30 are disposed on alternating and/or spaced apart vertebral levels of vertebrae V such that an instrument is disposed on every other vertebral level. In some embodiments, instruments 30 may be alternated and/or spaced apart over one or a plurality of vertebral levels of a treated section of vertebrae V.

An instrument release 32 of each instrument 30 is manipulated to move leg extensions 34 in an outward direction such that distal engagement parts 36 move outwardly and are disposed in an open position. Distal engagement parts 36 are brought into close proximity with receivers 16 of each of MAS 12 to provide engagement with each of MAS 12. Instrument release 32 is manipulated such that leg extensions 34 are moved inwardly and distal engagement parts 36 are disposed in a closed position to capture each of MAS 12 in releasable fixation. Leg extensions 34 define an opening, such as, for example, an elongated slot 38 that is disposed in alignment and communicates with passageway 22 to define a window 40.

Instruments 30 are applied to MAS 12 attached with levels T on portion LP, which includes a concave portion of vertebrae V. In some embodiments, instruments 30 are applied to MAS 12 attached with levels L on portion LP, which includes a convex portion of vertebrae V. In some embodiments, instruments 30 are applied to MAS 12 attached with levels T on portion CLP, which includes a convex portion of vertebrae V. In some embodiments, instruments 30 are applied to MAS 12 attached with levels L on portion CLP, which includes a concave portion of vertebrae V.

Spinal rod 14 extends between ends 42, 44 in a configuration for attachment with vertebrae V. Spinal rod 14 includes a portion 46 having a selected curvature. In one embodiment, spinal rod 14 has a concave configuration and is inserted into and provisionally disposed with MAS 12 and attached with levels T on portion LP, which includes a concave portion of vertebrae V.

In one embodiment, spinal rod 14 is sequentially inserted along vertebrae V and attached to MAS 12 at a plurality of vertebral levels. In one embodiment, spinal rod 14 is inserted in a cephalad to caudal orientation, in the direction shown by arrow AA in FIG. 3. In one embodiment, end 42 may be sharpened to facilitate insertion and movement through body B. In some embodiments, ends 42, 44 may include a locking element, such as, for example, a notch or groove, for attachment with an inserter 50 to maintain the orientation of spinal rod 14 relative to inserter 50 and/or vertebrae V during insertion and rotation of spinal rod 14.

Portion 46 is selectively pre-bent by the practitioner for correction of vertebrae V. In some embodiments, a rod template is disposed with body B to create a template for the pre-bent configuration of spinal rod 14 including the selected curvature of portion 46. In one embodiment, spinal rod 14 includes a pre-bent shape to apply specific corrective forces to the individual vertebral levels of vertebrae V. In one embodiment, the pre-bent configuration of spinal rod 14 and/or the selected curvature of portion 46 is determined by the flexibility of the spinal deformity and/or the amount of correction, translation and rotation of the vertebral levels of vertebrae V in an effort to align and correct the vertebral levels of vertebrae V. In some embodiments, spinal rod 14 and/or the selected curvature of portion 46 may be bent in one, two, or three dimensions depending on the amount of correction for the vertebral levels in the coronal, sagittal, and axial planes of vertebrae V.

Spinal rod 14 is attached with a distal end 51 of inserter 50 for insertion and positioning within body B, as shown in FIG. 5, and passing spinal rod 14 along instruments 30 and/or MAS 12. Inserter 50 includes a handle 52 such that spinal rod 14 is manipulated for insertion into body B, as shown in FIG. 3. End 42 is inserted into body B in a cephalad to caudal orientation, in the direction shown by arrow AA in FIG. 3, and through a window 40 of a first instrument 30/MAS 12 attached to a vertebral level V1. Spinal rod 14 is moved through window 40 of the first instrument 30/MAS 12 such that end 42 is sequentially inserted into and through a window 40 of a second instrument 30/MAS 12 attached to a vertebral level V2.

In some embodiments, insertion of end 42 into window 40 of the second instrument 30/MAS 12 may require spinal rod 14 and/or handle 52 to be rotated, in the direction shown by arrows BB in FIG. 4, and/or translated, in the direction shown by arrows CC and DD, relative to vertebrae V, due to the pre-bent configuration of spinal rod 14, the selected curvature of portion 46 and/or the curvature of vertebrae V. In some embodiments, spinal rod 14 and/or handle 52 may be rotated through a range of 0-180 degrees. Spinal rod 14 is similarly moved through windows 40 of third and fourth instruments 30/MAS 12 such that end 42 is sequentially inserted into and through the windows 40 of the third and fourth instruments 30/MAS 12 attached to vertebral levels V3, V4. In some embodiments, insertion of spinal rod 14 is performed percutaneously by manipulating handle 52 in a free hand delivery technique. In some embodiment, movement of spinal rod 14 through windows 40 and/or body B can be monitored using navigation, fluoroscopy imaging techniques and/or tactile feedback.

With inserter 50 attached and spinal rod 14 disposed in windows 40, as described herein, handle 52 is manipulated and spinal rod 14 is rotated and/or translated to a selected orientation relative to vertebrae V, which includes a selected sagittal and/or coronal rod position relative to vertebrae V, for correction of vertebrae V. Instruments 30 each include reducers 60, as shown in FIGS. 4 and 5, configured to dispose spinal rod 14 with receivers 16 of MAS 12. Each reducer 60 includes a handle 62 manipulable to align reducer 60 with an interior passageway of each of instruments 30. Reducer 60 has an outer surface 64 that is threaded with an inner surface of each of instruments 30. Reducer 60 is rotated to translate reducer 60 axially, in a proximal or distal direction relative to instrument 30. Reducer 60 is translated such that an end surface 66 engages spinal rod 14 in a configuration to move spinal rod 14 distally to drive spinal rod 14 into passageways 22 of receivers 16.

With inserter 50 attached and spinal rod 14 disposed in windows 40, as described herein, reducers 64 are manipulated to draw receivers 16 of MAS 12 attached with apical portion A, which includes levels V1, V2, V3, V4, up to receive spinal rod 14, in the direction shown by arrow EE in FIG. 5. Spinal rod 14 is selectively and provisionally reduced within passageways 22 such that spinal rod 14 is disposed in the selected orientation relative to vertebrae V, for example, in a sagittal plane of vertebrae V offset from plane SP for correction of vertebrae V.

Figure 6:
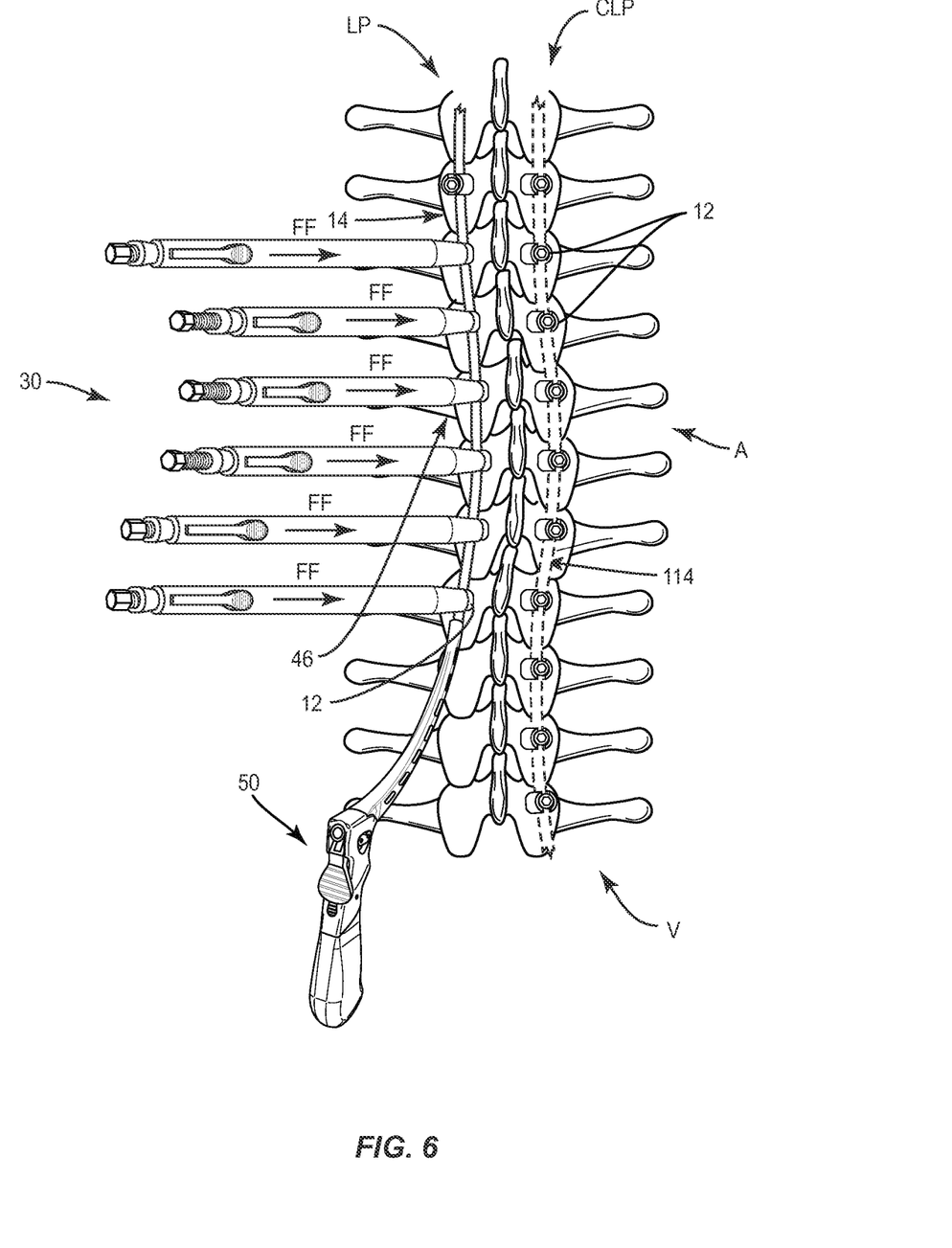
FIG. 6 is a plan view of components of the system and vertebrae shown in FIG. 3.
Figure 7:
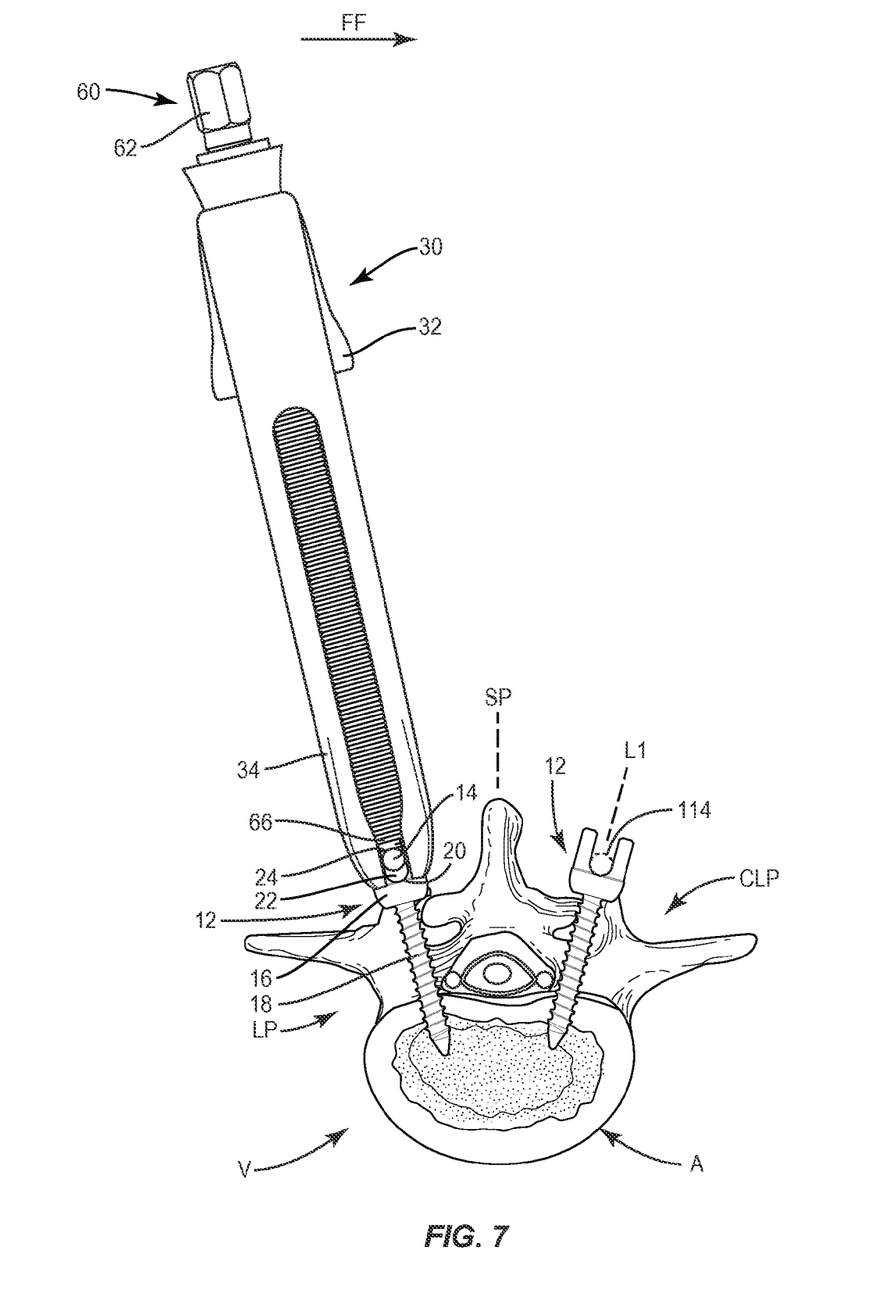
FIG. 7 is an axial view of components of the system and vertebrae shown in FIG. 3.

Spinal rod 14, as shown in FIGS. 6 and 7, is provisionally seated within receivers 16 connected with apical portion A such that inner surfaces 20 are movable relative to outer surface 24 and receivers 16 are movable relative to shafts 18. With inserter 50 attached with spinal rod 14 to maintain spinal rod 14 in the selected orientation, instruments 30 are manipulated, in the direction shown by arrows FF. Instruments 30 are movable to rotate receivers 16 about spinal rod 14 such that surface 20 rotates about surface 24. As surface 20 rotates about surface 24, receiver 16 pivots and/or rotates about shaft 18 to a movement limit at which point shaft 18, which are fastened with the vertebral levels adjacent apical portion A on portion LP, is caused to move about spinal rod 14. As such, manipulation of instruments 30, which are connected to shafts 18 fastened with adjacent apical portion A, provide a lever configuration or leverage for manipulation and resultant application of one or a plurality of forces and/or moments for application to vertebrae V, for example, a derotation force for a spinal treatment. In some embodiments, rotation of receiver 16 relative to shaft 18 causes apical portion A to move about spinal rod 14 into alignment with the selected orientation and the selected curvature of spinal rod. In some embodiments, movement of shaft 18 and apical portion A fastened therewith about spinal rod 14 causes apical portion A to move into alignment with the selected orientation and the selected curvature of spinal rod.

A force, in the direction shown by arrows FF, is applied to instruments 30 via manipulation of a practitioner during a surgical treatment, to displace, pull, twist or align vertebrae V to the selected orientation and the selected curvature of spinal rod 14 for sagittal, coronal and/or axial correction. Upon application of derotation forces to vertebrae V to the selected orientation and the selected curvature of spinal rod 14, as described, set screws are employed to finally lock spinal rod 14 with MAS 12 attached with portion LP adjacent apical portion A.

In some embodiments, intermediate portion 46 may be reduced, as described herein, with MAS 12 fastened with apical portion A and the remaining portions of spinal rod 14 reduced sequentially from portion 46 with MAS 12 fastened with vertebral levels extending in a cephalad and/or caudal direction from apical portion A. In some embodiments, instruments 30 are connected to MAS 12 fastened with vertebral levels extending in a cephalad and/or caudal direction from apical portion A and instruments 30 are manipulated, similar to that described, to create derotation forces and segmentally derotate the vertebral levels extending in a cephalad and/or caudal direction from apical portion A. In such embodiments, upon application of derotation forces to the vertebral levels extending in a cephalad and/or caudal direction from apical portion A to the selected orientation and the selected curvature of spinal rod 14, as described, set screws are employed to finally lock spinal rod 14 with MAS 12 attached with portion LP adjacent the vertebral levels extending in a cephalad and/or caudal direction from apical portion A.

In some embodiments, a spinal rod 114 (shown in phantom in FIGS. 6 and 7), having a selected curvature and disposed in a selected orientation relative to vertebrae V, as described herein, is attached with MAS 12 fastened with portion CLP of vertebrae V, similar to the methods described herein, for sagittal, coronal and/or axial correction of vertebrae V.

In some embodiments, reducers 60 may reduce spinal rod 14 with various MAS 12 incrementally, continuously to engagement with spinal rod 14 and/or to disengagement from spinal rod 14, during the various steps of the correction treatment. In some embodiments, the scoliosis correction method includes repeating the derotation method steps for other vertebrae. In some embodiments, the scoliosis correction method includes repeating the derotation method steps for vertebrae of the lumbar, cervical, thoracic and pelvic regions of a spinal column. In one embodiment, the scoliosis correction method is employed with a correction of a right thoracic adolescent idiopathic scoliosis. In one embodiment, the scoliosis correction method is employed with a correction of a left lumbar scoliosis.

In some embodiments, a guide wire and/or a trocar-cannula assembly may be employed as an instrument for gaining access to the surgical site and/or defining the pedicle trajectory. The guide wire is introduced along the pedicle trajectory before delivering the fasteners. The fasteners are translated over the guide wire to be delivered to vertebrae V. In one embodiment, an interbody implant (not shown) is delivered along a direct lateral surgical approach or pathway adjacent to a surgical site and implanted adjacent selected vertebral levels.

Upon completion of a procedure, described herein, the surgical instruments, assemblies and non-implanted components of spinal correction system 10 are removed and the incisions are dosed. One or more of the components of spinal correction system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal correction system 10. In some embodiments, spinal correction system 10 may include one or a plurality of plates, connectors and/or bone fasteners for use with a single vertebral level or a plurality of vertebral levels.

In one embodiment, spinal correction system 10 includes an agent, which may be disposed, packed, coated or layered within, on or about the components and/or surfaces of spinal correction system 10. In some embodiments, the agent may include bone growth promoting material, such as, for example, bone graft to enhance fixation of the components and/or surfaces of spinal correction system 10 with vertebrae. In some embodiments, the agent may include one or a plurality of therapeutic agents and/or pharmacological agents for release, including sustained release, to treat, for example, pain, inflammation and degeneration.

In some embodiments, the components of spinal correction system 10 may be employed to treat progressive idiopathic scoliosis with or without sagittal deformity in either infantile or juvenile patients, including but not limited to prepubescent children, adolescents from 10-12 years old with continued growth potential, and/or older children whose growth spurt is late or who otherwise retain growth potential. In some embodiments, the components of spinal correction system 10 and methods of use may be used to prevent or minimize curve progression in individuals of various ages.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A method for treating a spine, the method comprising the steps of:

fastening a plurality of fasteners with a lateral portion of vertebrae, each of the fasteners including a first element that defines an implant cavity and a second element configured for penetrating the vertebrae;

providing a longitudinal element including a portion having a selected curvature;

positioning the longitudinal element above the implant cavities;

rotating the longitudinal element about a longitudinal axis defined by the longitudinal element with the longitudinal element positioned above the implant cavities such that the portion is disposed in a selected orientation relative to the vertebrae;

reducing the longitudinal element into the implant cavities after the longitudinal element is rotated such that the portion is in the selected orientation relative to the vertebrae after the longitudinal element is reduced into the implant cavities; and moving the first element of at least one of the fasteners relative to the second element of the at least one of the fasteners such that the first element of at least one of the fasteners rotates relative to the portion and the second element of at least one of the fasteners moves about the longitudinal element to derotate the vertebrae while maintaining the portion in the selected orientation relative to the vertebrae.

2. A method as recited in claim 1, further comprising the step of percutaneously delivering the fasteners adjacent to a surgical site including the vertebrae.

3. A method as recited in claim 1, further comprising the step of connecting implant supports with the fasteners and the step of positioning includes passing the longitudinal element through the implant supports.

4. A method as recited in claim 1, further comprising the step of bending the portion to the selected curvature.

5. A method as recited in claim 1, wherein the selected orientation includes a sagittal plane of the vertebrae.

6. A method as recited in claim 1, further comprising the step of connecting a surgical instrument with the longitudinal element and the step of reducing includes manipulating the surgical instrument to fix the portion in the selected orientation.

7. A method as recited in claim 1, further comprising the step of connecting a surgical instrument with the longitudinal element and the step of positioning includes manipulating the surgical instrument to position the longitudinal element above the implant cavities.

8. A method as recited in claim 7, wherein the surgical instrument includes an inserter configured to percutaneously deliver the longitudinal element with a free hand technique.

9. A method as recited in claim 1, further comprising the step of connecting first portions of implant supports with the fasteners and the step of reducing includes rotating second portions of the implant supports relative to the first portions such that the second portions translate axially relative to the first portions and engage the longitudinal element thereby provisionally reducing the longitudinal element with the first elements.

10. A method as recited in claim 1, wherein the step of fastening includes fastening one or more of the fasteners with an apical portion of the vertebrae and the step of reducing includes reducing the longitudinal element with the fasteners fastened with the apical portion, and subsequently reducing the longitudinal element with the remaining fasteners sequentially from the apical portion.

11. A method as recited in claim 10, wherein the step of reducing the longitudinal element with the remaining fasteners includes sequential reduction from the apical portion in a cephalad and/or a caudal orientation.

12. A method as recited in claim 1, further comprising the step of connecting implant supports with the fasteners and the step of moving includes manipulating the implant supports to rotate the first elements relative to the portion such that the second elements derotate the vertebrae while maintaining the portion in the selected orientation.

13. A method as recited in claim 12, wherein rotation of the first elements derotate the vertebrae to correct the vertebrae in a sagittal plane of the vertebrae and/or a coronal plane of the vertebrae while maintaining the portion in the selected orientation.

14. A method as recited in claim 12, wherein the first element includes an inner surface that defines the implant cavity and the longitudinal element includes an outer surface such that the inner surface rotates about the outer surface.

15. A method as recited in claim 1, further comprising the step of locking the longitudinal element with the fasteners via coupling members with the portion disposed in the selected orientation.

16. A method as recited in claim 1, further comprising the steps of fastening one or more of the fasteners with a contra-lateral portion of the vertebrae and disposing a second longitudinal element with the fasteners fixed with the contra-lateral portion.

17. A method for treating a spine, the method comprising the steps of:
fastening a plurality of fasteners with a lateral portion of vertebrae, each of the fasteners including a receiver that defines an implant cavity and a shaft configured for penetrating the vertebrae;
providing a longitudinal element including a portion having a selected curvature;
connecting a surgical instrument to the longitudinal element;
manipulating the surgical instrument to position the longitudinal element above the implant cavities;
rotating the longitudinal element about a longitudinal axis defined by the longitudinal element with the longitudinal element positioned above the implant cavities such that the portion is disposed in a selected orientation relative to the vertebrae;
reducing the longitudinal element within at least one of the implant cavities after the longitudinal element is rotated such that the portion is in the selected orientation relative to the vertebrae after the longitudinal element is reduced into the implant cavities; and
rotating the receiver of at least one of the fasteners relative to the shaft of the at least one of the fasteners such that the receiver of at least one of the fasteners rotates relative to the longitudinal element and the shaft of at least one of the fasteners moves about the longitudinal element to derotate the vertebrae while maintaining the portion in the selected orientation relative to the vertebrae.

18. A method as recited in claim 17, further comprising the step of connecting implant supports with the fasteners and the step of manipulating includes provisionally reducing the longitudinal element within the implant supports.

19. A method as recited in claim 17, wherein the surgical instrument includes an inserter configured to percutaneously deliver the longitudinal element with a free hand technique.

20. A method for treating a spine, the method comprising the steps of:
fastening a plurality of fasteners with a lateral portion of vertebrae, each of the fasteners including a receiver having an inner surface that defines an implant cavity and a shaft configured for penetrating the vertebrae, the receiver being rotatable relative to the shaft in a plurality of planes that lie in a cone configuration, wherein one or more of the fasteners are fastened with an apical portion of the vertebrae;
providing a longitudinal element including a portion having a selected curvature;
positioning the longitudinal element above the fasteners;
rotating the longitudinal element about a longitudinal axis defined by the longitudinal element with the longitudinal element positioned above the implant cavities such that the portion is disposed in a selected orientation relative to the vertebrae, the fasteners being disposed with the apical portion;
reducing the longitudinal element into the implant cavities after the longitudinal element is rotated such that the longitudinal element is in the selected orientation relative to the vertebrae after the longitudinal element is reduced into the implant cavities; and
rotating the receivers relative to the portion and the shafts such that the inner surfaces rotate relative to an outer surface of the longitudinal element and the shafts move about the longitudinal element to derotate the vertebrae while maintaining the portion in the selected orientation relative to the vertebrae.

\* \* \* \* \*

UNITED STATES PATENT AND TRADEMARK OFFICE
CERTIFICATE OF CORRECTION

PATENT NO.      : 9,717,531 B2
APPLICATION NO. : 14/057930
DATED           : August 1, 2017
INVENTOR(S)     : Anand et al.

Page 1 of 1

It is certified that error appears in the above-identified patent and that said Letters Patent is hereby corrected as shown below:

On the Title Page

In Item (72), under "Inventors", in Column 1, Line 2, delete "R" and insert -- R. --, therefor.

In the Specification

In Column 1, Line 4, delete "HELD" and insert -- FIELD --, therefor.

In Column 1, Line 34, delete "of;" and insert -- of: --, therefor.

In Column 5, Line 19, delete "Inc)," and insert -- Inc.), --, therefor.

In Column 5, Line 42, delete "polyiyrosine carbonate, polycaroplaetohe" and insert -- polytyrosine carbonate, polycaprolactone --, therefor.

In Column 6, Line 7, delete "distracters," and insert -- distractors, --, therefor.

In Column 10, Line 36, delete "reducers 64" and insert -- reducers 60 --, therefor.

In Column 12, Line 1, delete "dosed." and insert -- closed. --, therefor.

Signed and Sealed this
Sixth Day of February, 2018

Joseph Matal
*Performing the Functions and Duties of the*
*Under Secretary of Commerce for Intellectual Property and*
*Director of the United States Patent and Trademark Office*